United States Patent [19]

Okuda

[11] Patent Number: 4,762,131
[45] Date of Patent: Aug. 9, 1988

[54] DRILLER PROVIDING LIGHT AND SOUND STIMULI FOR STIMULATING THE VISUOSENSORY AND AUDIOSENSORY NERVES, FOR USE IN THE REHABILITATION OF POSTAPOPLECTIC PARALYTIC PATIENTS

[76] Inventor: Shigeru Okuda, 22-13, Senju-Akebonocho, Adachi-ku, Tokyo, Japan

[21] Appl. No.: 849,407

[22] Filed: Apr. 8, 1986

[30] Foreign Application Priority Data

Sep. 2, 1985 [JP] Japan .............................. 60-133159[U]

[51] Int. Cl.$^4$ ....................... F21V 33/00; A61N 00/00
[52] U.S. Cl. .................................... 128/396; 128/395; 362/85; 434/258
[58] Field of Search ........................ 128/396, 395, 745; 340/326, 815.21, 815.22; 434/221, 258; 362/85, 130, 131, 132, 133

[56] References Cited

U.S. PATENT DOCUMENTS

| | | | |
|---|---|---|---|
| 2,023,488 | 12/1935 | Poppen | 434/258 |
| 2,301,911 | 11/1942 | Lootens et al. | 340/326 |
| 3,631,235 | 12/1971 | Odermann | 362/133 |
| 3,657,456 | 4/1972 | Kozak | 434/258 |
| 4,004,143 | 1/1977 | Good et al. | 362/131 |
| 4,028,819 | 6/1977 | Walker | 434/258 |
| 4,233,649 | 11/1980 | Scheer et al. | 362/131 |
| 4,321,717 | 3/1982 | Serra | 362/131 |

FOREIGN PATENT DOCUMENTS 1187785 10/1985 U.S.S.R. .............................. 128/745

*Primary Examiner*—Carl D. Friedman
*Assistant Examiner*—Michael Safavi
*Attorney, Agent, or Firm*—Holman & Stern

[57] ABSTRACT

A driller device provides controlled intermittent light and sound stimuli for stimulating the visuosensory and audiosensory nerves in the rehabilitation of postapoplectic paralytic patients. Two light emitters are alternately intermittently turned on to stimulate the visual nerves of a postapoplectic patient. Also, electronic buzzers are intermittently operated for sound generation to stimulate the hearing nerves of the patient.

4 Claims, 4 Drawing Sheets

DRILLER PROVIDING LIGHT AND SOUND STIMULI FOR STIMULATING THE VISUOSENSORY AND AUDIOSENSORY NERVES, FOR USE IN THE REHABILITATION OF POSTAPOPLECTIC PARALYTIC PATIENTS

BACKGROUND OF THE INVENTION (a) Field of the Invention

This invention relates to a driller used in rehabilitation for recovering the function of a paralyzed body part of a postapoplectic paralytic patient.

(b) Prior Art

When some nerve cells are damaged by brain apoplaxy, part of the body is paralyzed. In such a case, rehabilitation for recovering the function of the paralyzed part is usually done through passive drilling with the aid of a physical therapist.

However, after the lapse of one year from the start of rehabilitation, there comes a limit of the recovery of the body function because the recovery is prevented by the loss of grain nerves. Most postapolectic patients, therefore, can not completely recover the body function so that they have to live the rest of their life with paralyzed arms, hands, fingers, etc.

A man feels an excitement or moves the body through the following process.

The nerve system consists of numerous neurons as units of a nerve system;. These neurons form complicated linkages. An external stimulation is sensed when a neuron linkage that transmits the stimulation reaches the cerebral cortices. Also, transmission of a stimulation toward distal portions becomes a conscious motion when the stimulation is generated from the cerebral cortices.

Therefore, if motor nerves are damaged (or broken) due to brain apoplexy or like cause, there appears an obdormission. If it is possible that brain nerves can join by bypassing a damaged portion, the recovery of the function of the overall body can be expected. When some nerve cells are broken by some cause, they can not be repaired. However, when nerve tissues are broken, reproduction of tissues from the broken end near cells occurs, and the new nerves grow to restore the initial nerve fibers. Various stimulations are transmitted through the nerve system with the formation of neuron linkages which join together through synapses. When nerve fibers are reproduced, the nerve system receives the external stimulation to make active the neuron linkages. At the same time, if it is intended to move a paralyzed part of the body by the patient's own will, the intended function is eventually transmitted to the cerebral cortices and appears as conscious motion.

SUMMARY OF THE INVENTION

The invention is predicated in the fact that the nerve fibers can be reproduced, and it is based on the concept that the patient's act of self-guidance (i.e., an intent of causing a conscious motion of the body, the function of which is to be recovered) without help of others but by the patient's own solitary will with the visual and hearing nerves stimulated with intermittent light and electronic sound, respectively, will make neuron linkages active and permit recovery of the function of the paralyzed part of the body.

An object of the invention, accordingly, is to permit recovery of the function of a paralyzed part of the body of a postapoplectic paralytic patient.

Another object of the invention is to permit recovery of the function of a paralyzed part of the body of a post-apoplectic paralytic patient through drilling without the help of any other person such as a physical therapist but by the patient's own will and thereby stimulating the brain nerve cells.

A further object of the invention is to permit recovery of the function of a paralyzed part of the body of a post-apoplectic paralytic patient by making neuron linkages active through the patient's self-guidance with the visual and hearing nerves stimulated with intermittent light and electronic sound, respectively.

DETAILED DESCRIPTION OF THE PREFERRED EMBODIMENTS

Figure 1:
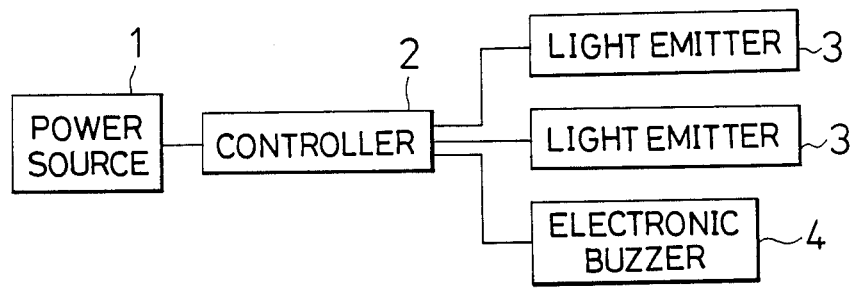
FIG. 1 is a block diagram illustrating a system underlying the invention.

FIG. 1 is a block diagram schematically illustrating the system underlying the invention. Power source 1 is connected through controller 2 to two light emitters 3 and an electronic buzzer 4. Controller 2 includes intermittently on-off operated switch means for intermittently operating light emitters 3 or buzzer 4.

Figure 2:
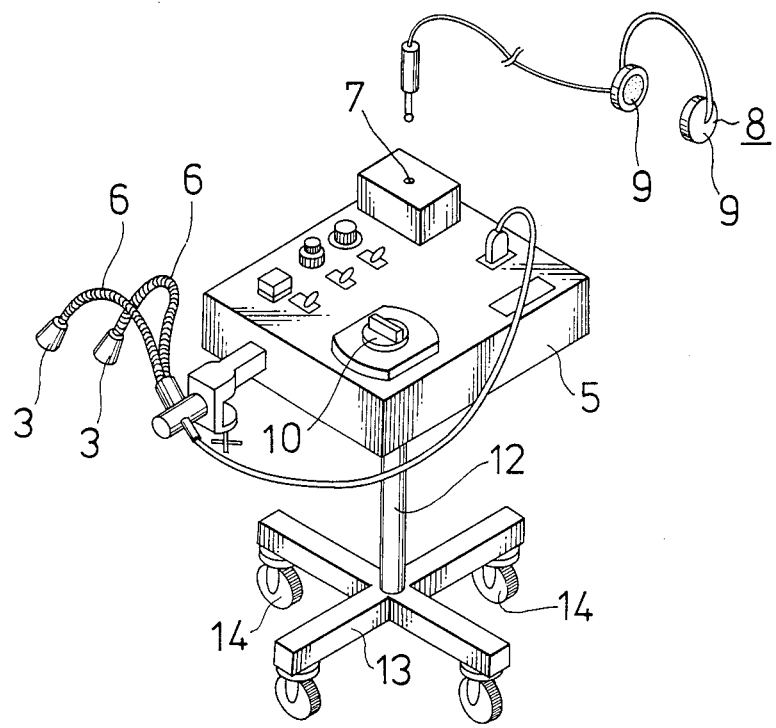
FIG. 2 is a perspective view showing an embodiment of the driller according to the invention.

FIG. 2 is a perspective view showing an embodiment of the invention. Referance numeral 5 designates a control section body, which has a horizontal flat rectangular shape and accommodates controller 2 for providing light and sound signals. Two flexible arms 6 capable of being bent are supported on one side of control section body 5. Light emitters 3 are installed at the free ends of flexible arms 6. Flexible arms 6 have their stems secured to control section body 5.

The illumination intensity of light emitted from light emitters 3 should be such that the light is at least glaring to the patient whose eyes are at a distance of 20 to 30 cm from the light sources and nevertheless has no harmful effects. The light intensity which is glaring to the patient's eyes varies with individual and also depending on the surrounding environments. Therefore, light emitters 3 are suitably selected from among light sources which emit light of 400 to 2,000 lm. The inventor used an incandescent lamp for the illumination purposes with ratings of 100V and 60V (790 lm), and an illumination intensity of 300 to 1,000 lm could be obtained in the neighborhood of the patient's face, this illumination intensity being recognized to be particularly effective for the stimulation of the patient's visuosensory nerves.

Power supply connector 7 is provided on top of control section body 5. A plug, to which headphone 8 is connected via a cord, is inserted into power supply connector 7. Headphone 8 has opposite ear pads 9, in each of which an electronic buzzer 4 is installed.

Electronic buzzer 4 is a contactless system unlike a mechanical buzzer which has electric contacts. Also, its reproducing capacity is centered on the neighborhood of the input signal frequency, so that is is highly efficient. For the above reasons, the sound quality of the electronic buzzer is very effective for the stimulation of the patient's visuosensory nerves. Generally, man is most sensitive to frequencies of 1 to 3 kHz. These frequencies thus can sufficiently stimulate the audiosensory nerves of hearing. In order to provide sound having a magnitude, which is sufficient to stimulate the patient's audiosensory nerves while giving no mental pain, it is necessary to install a buzzer, which produces sound of 50 to 90 phones (at a distance of 1 m) at the ear. The inventor recognized that an electronic buzzer, which has a frequency of 2 or 3 kHz and provides a sound volume of 70 phones (at a distance of 1 m) was effective for stimulation of the patient's audiosensory nerves.

Reference numeral 10 designates a manual knob of a timer 11 which can provide a preset timer period until a switch is turned off.

Vertical support rod 12 extends from the center of the underside of control section body 5. Legs 13 are provided on the lower end of support rod 12 and carry wheels 14 provided at their end so that they can be freely moved.

Figure 3:
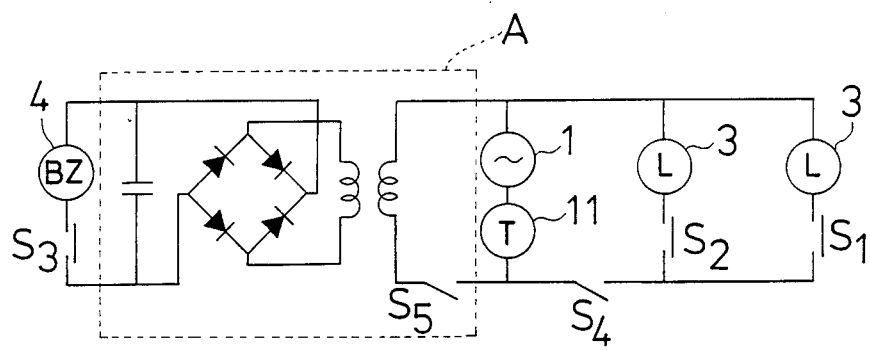
FIG. 3 is a circuit diagram showing the electric circuit of the embodiment.

FIG. 3 shows the electric circuit of the embodiment. Timer 11 is connected in series with AC power source 1. Two light emitters 3 are connected in parallel with the series combination of power source 1 and timer 11 via respective switches $S_1$ and $S_2$. Power source rectifier circuit A is connected across the combination of power source 1 and timer 11 to obtain a DC output. Electronic buzzer 4 is connected between DC output terminals via switch $S_3$ which is connected to controller 2. Switch $S_4$ is provided between light emitters 3 and power source 1, and switch $S_5$ is provided between electronic buzzer 4 and power source 1.

Figure 4:
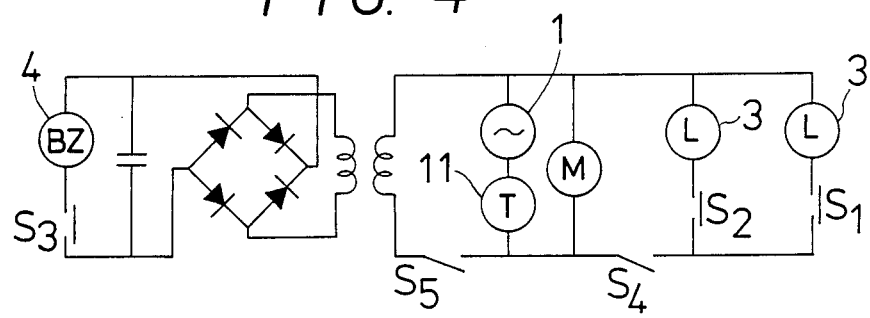
FIG. 4 is a circuit diagram showing an example of the electric circuit where a motor is used for a controller with intermittently on-off operated switch means according to the invention.

FIG. 4 is a circuit diagram showing an example of the electric circuit where a motor with cam is used for controller 2 with intermittently on-off operated switch means for intermittently on-off operating switches $S_1$ to $S_3$. As is shown, motor M is connected in parallel with the combination of power source 1 and timer 11 and also with the combinations of light emitters 3 and switches $S_1$ and $S_2$. Switches $S_1$ to $S_3$ are microswitches. Switches $S_1$ and $S_2$ are for on-off operating the light emitters. Switch $S_3$ is for on-off operating the electronic buzzer.

Figure 5:
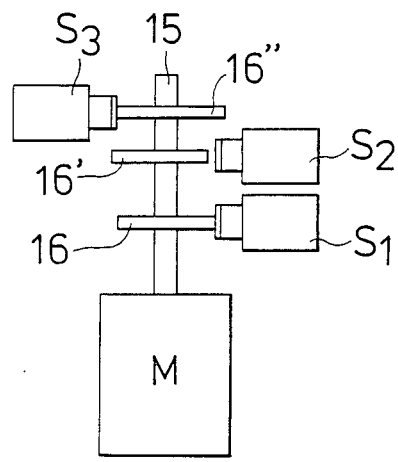
FIG. 5 is a plan view showing the configuration when a motor is used for the controller shown in FIG. 4 with intermittently on-off operated switch means according to the invention.

FIG. 5 is a plan view showing an arrangement, in which the microswitches are on-off operated by cams. Shaft 15 of motor M has cams 16, 16' and 16" secured to it. Microswitches $S_1$ to $S_2$ are turned on when they are urged by a protruding portion of respective cams 16, 16' and 16".

Two cams 16 and 16' having the same size and secured at different phase angles to shaft 15 of motor M correspond to microswitches $S_1$ and $S_2$ of light emitters 3. In this case, two light emitters 3 are turned on alternately. Also, electronic buzzer 4 is on-off operated with microswitch $S_3$ depressed with protruding portion of cam 16". The interval or pitch of the intermittent light or sound generation can be controlled by controlling the revolving rate of motor M.

Figure 6:
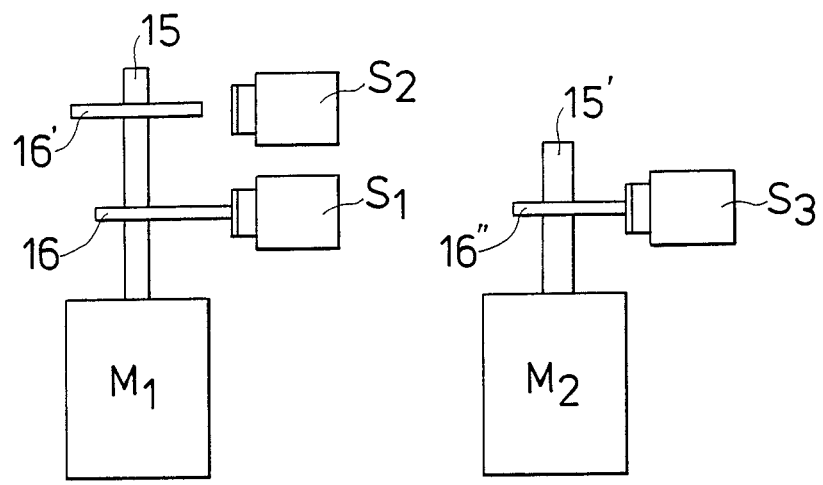
FIG. 6 is a plan view showing a modification of the controller where two motors are used.

FIG. 6 shows a modification of the arrangement of FIG. 5 with three cams 16, 16' and 16" mounted on shaft 15 of a single motor M. In the arrangement of FIG. 6, two motors $M_1$ and $M_2$ are provided. Two cams 16 and 16' for intermittently operating light emitters 3 are mounted on shaft 15 of motor $M_1$, while cam 16" for intermittently operating electronic buzzer 4 is mounted on shaft 15' of motor $M_2$. With this arrangement, the same effect can be obtained.

Further, mechanical means of motor and cam shown in FIGS. 5 and 6, as controller 2 having intermittently on-off operated switch means, may be replaced with electrical means.

More specifically, switches $S_1$ to $S_3$ may be intermittent switches using electronic circuits such as oscillators and logic circuits.

Figure 7:
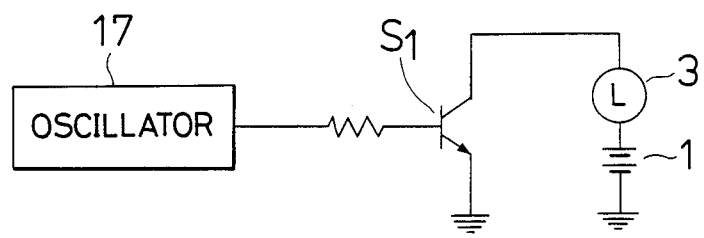
FIG. 7 is a circuit diagram showing a further modification of the controller which consists of an oscillator and a semiconductor switch.

FIG. 7 is a view showing an example of controller 2 with intermittently on-off operated switch means, in which switch $S_1$ is constituted by electrical means.

Figure 8:
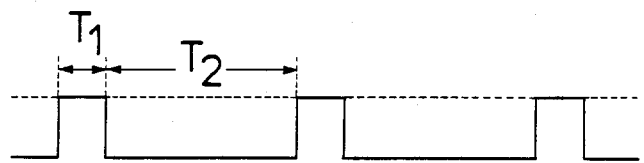
FIG. 8 is a waveform diagram showing an output waveform of the oscillator.

Oscillator 17 is a non-stable multi-vibrator which produces a waveform as shown in FIG. 8 having a long cycle period. Periods $T_1$ and $T_2$ are determined by the values of resistor and capacitor connected to the base of two transistors of a multi-vibrator. Semiconductor switch $S_1$ consists of a transistor, the collector-to-emitter path of which is connected across light emitter 3 and power source 1. The output of oscillator 17 is applied to the base of the transistor of semiconductor switch $S_1$. Thus, when a rectangular wave is generated, a base current is caused to flow through semiconductor switch $S_1$, thus turning on the transistor. Current is thus caused to flow from the power source 1 to light emitter 3, so that light is emitted from light emitter 3. When the output of oscillator 17 is zero, no base current flows through semiconductor switch $S_1$, so that the transistor is "off". No current thus is supplied from power source 1 to light emitter 3.

Switches $S_2$ and $S_3$ of controller 2 have the same construction as switch $S_1$, consisting of an oscillator and a semiconductor switch. Switches $S_1$ to $S_3$ are individually on-off controlled by respective oscillators. Thus, by varying the period $T_2$ of the oscillation output shown in FIG. 8, two light emitters 3 generate light substantially alternately, while electronic buzzer 4 generates sound with a constant cycle period independently of the light generation of light emitters 3.

Figure 9:
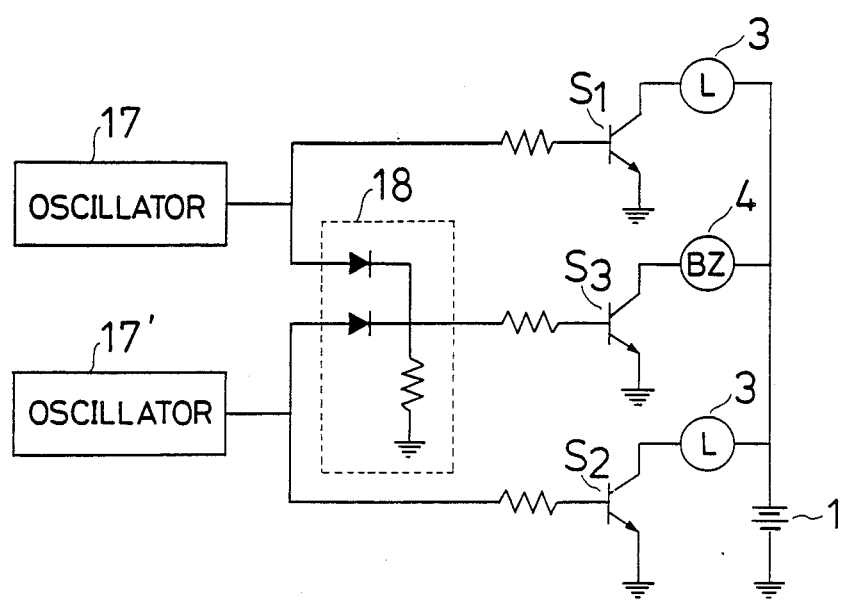
FIG. 9 is a circuit diagram showing a different electric circuit according to the invention, which has a controller for synchronizing the light generation of light emitters and sound generation of an electronic buzzer.

FIG. 9 shows a circuit, which uses two non-stable multi-vibrators having different oscillation frequencies, and in which the sound of electronic buzzer 4 is synchronized to the light generation of light emitters 3.

The output of oscillator 17 is coupled to the base of the transistor of semiconductor switch $S_1$, the output of oscillator 17' having a different oscillation frequency from that of oscillator 17 which is connected to the base of the transistor of semiconductor switch $S_2$.

The outputs of oscillators 17 and 17' are coupled to logic circuit 18 (i.e., OR gate) consisting of diodes and a resistor, and the output of logic circuit 18 is coupled to the base of the transistor of semiconductor switch $S_3$ connected to the power source.

With the above construction, when there is an output waveform of either oscillator 17 or 17', semiconductor switch $S_3$ is "on", and electronic buzzer 4 generates sound in synchronism to the light generation of light emitters 3. In the instances of FIGS. 7 and 8, a DC power source is used, and also DC power sources are used for light emitters 3.

The driller according to the invention is used as follows.

The patient is seated on a chair or laid down on a bed near the driller. Light emitters 3 are then secured in positions in front of and slightly above the eyes of the patient facing the front. At this time, light emitters 3 can be secured in positions suitable for stimulating the patient's sense of sight. It is recommended to set the distance between light emitters 3 and patient's eyes to be 20 to 30 cm.

Then, headphone 8, the plug of which is mounted in power source connector 7, is set on the patient's ears.

A drilling time is then set by operating knob 10 of timer 11, and switch $S_4$ for the patient's light emitters and switch $S_5$ for the electronic buzzer are turned on.

Since light emitters 3 and electronic buzzer 4 are provided with independent switches, either the former or the latter alone may be operated for the drilling.

The patient then tries to self-guide himself or herself in an effort to move the paralyzed part of the body by the own will with the visual and hearing nerves stimulated by the combination of the intermittent light and electronic sound. With the repetition of this drill, the nerve cell neuron linkages are made active to form new nerve paths bypassing the damaged part. It is thus possible to recover the function of the paralized part of the body.

As has been described in the foregoing, with the above construction according to the invention light and electronic sound serve as special stimulation best suited to the nerves, that is, they serve as a trigger of making active neuron linkages of the nerves necessary for the movement of an intended part of the body without the need of others such as a physical therapist but by the patient's own will. It is thus possible to recover the function of the paralyzed part of the body by drilling while being stimulated. Further, a greater effect can be expected when the driller according to the invention is used in combination with conventional rehabilitation.

What is claimed is:

1. A driller device for providing light and sound stimuli for stimulating the visuosensory and audiosensory nerves of a postapoplectic paralytic patient, comprising two light emitters each capable of emitting light of 400 to 2,000 lm for stimulating the visuosensory nerves, said light emitters each being installed at an end of each of a pair of flexible arms each secured at a stem thereof to a control section body, said light emitters being connected to a power source through a controller provided in the control section body, the controller having intermittently on-off operated switch means, and electronic buzzers capable of producing an acoustical output of 50 to 90 phons for stimulating the audiosensory nerves, said electronic buzzers being installed in ear pads of a headphone connected to said control section body, said electronic buzzers being connected to said power source through said controller.

2. A driller device according to claim 1, wherein said controller having said intermittently on-off operated switch means includes a motor and three cams secured at different phase angles to a shaft of said motor, said cams being capable of depressing two corresponding switches for light emitter light generation control and one corresponding switch for electronic buzzer sound generation control, respectively.

3. A driller device according to claim 1, wherein said controller having said intermittently on-off operated switch means includes two motors, two cams secured at different phase angles to a shaft of one of said motors and capable of respectively depressing two corresponding switches for light emitter light generation control, and a third cam secured to a shaft of the other one of said motors and capable of depressing a third switch for electronic buzzers sound generation control.

4. A driller device according to claim 1, wherein said controller with said intermittently on-off operated switch means includes a plurality of semiconductor switches for effecting on-off control of corresponding ones of said light emitters and electronic buzzers, said semiconductor switches receiving respective rectangular wave signals from a plurality of oscillators having different oscillation frequencies.

* * * * *